(12) United States Patent
Matzinger et al.

(10) Patent No.: US 7,070,564 B2
(45) Date of Patent: Jul. 4, 2006

(54) DEVICES FOR PHYSIOLOGICAL FLUID SAMPLING AND METHODS OF USING THE SAME

(75) Inventors: David Matzinger, Menlo Park, CA (US); Khalid R. Quraishi, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 10/995,688

(22) Filed: Nov. 22, 2004

(65) Prior Publication Data

US 2005/0113717 A1      May 26, 2005

Related U.S. Application Data

(63) Continuation of application No. 09/974,654, filed on Oct. 10, 2001, now Pat. No. 6,939,310.

(51) Int. Cl.
 *A61B 5/00* (2006.01)
(52) U.S. Cl. .................. 600/300; 600/309; 600/504
(58) Field of Classification Search ..................... None
 See application file for complete search history.

(56) References Cited

U.S. PATENT DOCUMENTS

| | | | | |
|---|---|---|---|---|
| 3,782,365 | A | * | 1/1974 | Pinna .................. 600/481 |
| 3,998,210 | A | * | 12/1976 | Nosari .................. 600/549 |
| 4,175,543 | A | * | 11/1979 | Suzuki et al. ............ 600/549 |
| 4,476,877 | A | | 10/1984 | Barker |
| 4,667,679 | A | * | 5/1987 | Sahota .................. 600/407 |
| 5,261,409 | A | | 11/1993 | Dardel |
| 5,349,954 | A | | 9/1994 | Tiemann et al. |
| 5,373,858 | A | | 12/1994 | Rose et al. |
| 5,452,716 | A | | 9/1995 | Clift |
| 5,519,208 | A | | 5/1996 | Esparza et al. |
| 5,551,424 | A | | 9/1996 | Morrison et al. |
| 5,617,852 | A | | 4/1997 | MacGregor |
| 5,682,233 | A | | 10/1997 | Brinda |

(Continued)

FOREIGN PATENT DOCUMENTS

DE      198 18 532      10/1998

(Continued)

OTHER PUBLICATIONS

Berardesca et al. Bioengineering of the Skin; Cutaneous Blood Flow and Erythmea, CRC Press, Chapter 1-3 (1995).

(Continued)

*Primary Examiner*—Robert L. Nasser
*Assistant Examiner*—Patricia C. Mallari
(74) *Attorney, Agent, or Firm*—Kagan Binder, PLLC (57) ABSTRACT

Methods and devices are provided for determining a suitable site for sampling physiological fluid. In the subject methods, a potentially suitable physiological sampling site is selected, the fluid flow of the site is characterized and the site is then determined to be suitable based on the whether the site has high or low flow. Suitability may also be determined based on the type of sample obtainable from the site, where the order of the above-described steps may be altered. The subject devices include at least one site flow characterization element for determining the flow characteristics of a potential physiological sampling site and/or at least one sample type characterization element for determining whether the vasculature is arterial, venous or neither, i.e., an interstitial fluid sampling site. The subject methods and devices are particularly suited for use in the detection of physiological sampling sites in the fingers, arms, legs, earlobes, heels, feet, nose and toes. Also provided are kits that include the subject devices for use in practicing the subject methods.

18 Claims, 4 Drawing Sheets

U.S. PATENT DOCUMENTS

| | | | |
|---|---|---|---|
| 5,728,074 A * | 3/1998 | Castellano et al. | 604/207 |
| 5,769,791 A | 6/1998 | Benaron et al. | |
| 5,830,137 A | 11/1998 | Scharf | |
| 5,833,602 A | 11/1998 | Osemwota | |
| 5,951,492 A | 9/1999 | Douglas et al. | |
| 5,972,294 A | 10/1999 | Smith et al. | |
| 6,048,312 A | 4/2000 | Ishrak et al. | |
| 6,099,484 A | 8/2000 | Douglas et al. | |
| 6,104,939 A | 8/2000 | Groner et al. | |
| 6,122,535 A | 9/2000 | Kaestle et al. | |
| 6,126,600 A | 10/2000 | Oxaal et al. | |
| 6,144,867 A | 11/2000 | Walker et al. | |
| 6,151,107 A | 11/2000 | Schollermann et al. | |
| 6,163,715 A | 12/2000 | Larsen et al. | |
| 6,167,297 A | 12/2000 | Benaron | |
| 6,178,340 B1 | 1/2001 | Svetliza | |
| 6,178,342 B1 | 1/2001 | Borgos et al. | |
| 6,230,035 B1 | 5/2001 | Aoyagi et al. | |
| 6,230,046 B1 | 5/2001 | Crane et al. | |
| 6,264,611 B1 | 7/2001 | Ishikawa et al. | |
| 6,332,871 B1 * | 12/2001 | Douglas et al. | 600/583 |
| 6,336,899 B1 | 1/2002 | Yamazaki | |
| 6,374,128 B1 | 4/2002 | Toida et al. | |
| 6,463,309 B1 * | 10/2002 | Ilia | 600/310 |
| 6,464,646 B1 * | 10/2002 | Shalom et al. | 600/549 |

FOREIGN PATENT DOCUMENTS

| | | |
|---|---|---|
| WO | WO 98/20794 | 5/1998 |

OTHER PUBLICATIONS

Nilsson, G. et al. "Laser Doppler Flowmetry-A New Technique for Noninvasive Assessment of Skin Blood Flow," Cosmetics & Toiletries, vol. 99:97-108, Mar. 1984.

* cited by examiner

Optimal Measurements

| | Flow Characterization | | Sample Type Characterization | | |
|---|---|---|---|---|---|
| | Temperature | RBC Flux | Pulse | HbO/Hb | Total Hb |
| 1. large volume arterial/capillary | MAX | MAX | MAX | MAX | MAX |
| 2. large volume venous | MAX | MAX | MIN | MIN | MAX |
| 3. interstitial fluid | MIN | MIN | MIN | — | — |

MAX: Maximum values or high values
MIN: Minimum values or low values

DEVICES FOR PHYSIOLOGICAL FLUID SAMPLING AND METHODS OF USING THE SAME

CROSS-REFERENCE TO RELATED APPLICATIONS

This application is a continuation of U.S. patent application Ser. No. 09/974,654, filed Oct. 10, 2001 now U.S. Pat. No. 6,939,310, herein incorporated by reference in its entirety.

FIELD OF THE INVENTION

The field of this invention is physiological fluid sampling and more particularly devices and methods of use thereof for non-invasively determining suitable physiological fluid sampling sites.

BACKGROUND OF THE INVENTION

Analyte concentration characterization in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration characterization, a variety of analyte concentration characterization protocols and devices for both clinical and home testing have been developed.

To determine the concentration of an analyte in a physiological sample, a physiological sample must first be obtained from a site suitable for the particular test to be performed on the sample. For example, certain tests require a specific volume of interstitial fluid as the sample and others require a specific volume of blood, blood derivatives and the like as the sample. As such, depending on the type of sample required by the test, a site which expresses the requisite volume of the particular sample type must first be located.

The current processes of physiological fluid sample collection have certain drawbacks. First and foremost, such processes or techniques are associated with a significant amount of pain. Furthermore, a patient may need to endure multiple skin-piercings in order to find one suitable sampling site or enough sites to collect the requisite amount of sample. The pain associated with sample collection may have serious adverse consequences for those who require analyte characterizations to be performed, e.g., analyte detection and/or concentration determinations. For instance, patients who require frequent analyte concentration determinations may not adhere to their requisite testing protocols due to this associated pain and it is not uncommon for patients who require frequent monitoring of an analyte to simply avoid monitoring the analyte of interest because of the pain involved in sample collection. With diabetics, for example, the failure to measure their glucose level on a prescribed basis results in a lack of information necessary to properly control the level of glucose. Uncontrolled glucose levels can be very dangerous and even life threatening.

Typically, and more typically for those performing home testing protocols, common sampling sites include the fingers. Recently however, the arm has become a popular alternative sampling site because its nerve beds are sparser than in the fingers, thus minimizing pain somewhat. However, collecting a physiological fluid sample from the arm has disadvantages as well. Most notably, there are particular anatomical and physiological aspects of the arm which make physiological fluid collection from it difficult.

Small veins and arteries typically reach to within about 1 mm of the surface of the skin; arterioles ascend vertically from these to within about 0.5 mm of the surface where they branch out and become capillaries which reach to within about 0.25 mm of the surface. The capillaries terminate in venuoles which carry blood back to veins. Each ascending arteriole feeds a maze of branched arterioles, capillaries and venuoles, where each groupings of capillaries, venuoles and arterioles have horizontal dimensions on the order of about 2–7 mm. Skin piercing to obtain blood from these structures is usually done to a depth of about 1 mm or less. Spaces exist between these areas where the arterioles, venuoles and capillaries are non-existent, sparse or not sufficiently engorged with blood.

When randomly choosing a sampling site, a patient may encounter a substantially high fluid flow area or a substantially low fluid flow area. Oftentimes, an adequate or minimum volume of sample is required in order to perform a particular test accurately. Thus, if such a minimum volume were not collected from a first skin piercing, the patient would be required to continually pierce the skin until the minimum volume were obtained. It can be appreciated that this process of multiple skin piercings would contribute to more pain to the patient.

Furthermore, certain tests require a particular sample type in order to perform an accurate test. However, when randomly choosing a site to pierce the skin, a patient may encounter (1) a region with substantially few or no arteries or veins, and thus a good source of interstitial fluid, but not a good source of arterial or venous blood, (2) a region rich in arteries and thus a good source of arterial blood, but not a good source of venous blood or interstitial fluid, (3) a region rich in veins and thus a good source of venous blood, but not a good source of arterial blood or interstitial fluid, and (4) a combination of 1–3 which may not be suitable for any test. Blood from capillaries tends to be arterial in nature. Thus, if sample is ultimately obtained from a site such as site (1) above for a test which requires a blood sample, i.e., a site with few or no sources of arterial or venous blood, the sample may be diluted with or composed entirely of interstitial fluid which may skew results of the particular test. For instance, it is known that arterial samples, venous samples and interstitial fluid samples may have different analyte concentrations, e.g., arterial blood can have as much as 7 mg/dl higher glucose levels than does venous blood. Thus, it can be appreciated that the ability to choose a suitable sampling site is very important. Furthermore, if a type of sample is obtained that is not appropriate for a particular testing protocol, the patient may be required to pierce the skin additional times, again contributing more pain to the patient.

As such, there is continued interest in the development of new devices and methods for use for non-invasively determining whether, once the skin is pierced, the patient will be able to obtain the appropriate sample volume from the site for the particular test to be performed and also whether an appropriate sample type can be obtained from the site. Of particular interest would be the development of such devices, and methods of use thereof, which are efficient and simple to use. Such devices integrated with at least one skin-piercing element for piercing the skin once an appropriate sampling site has been non-invasively determined and/or integrated with a reagent test strip for determining the concentration of an analyte in the sample would also be of particular interest.

SUMMARY OF THE INVENTION

Methods and devices are provided for determining a suitable site for sampling physiological fluid. In the subject methods, a potentially suitable physiological sampling site is selected, the fluid flow of the site is characterized and the site is then determined to be suitable based on the whether the site has high or low flow. Suitability may also be determined based on the type of sample obtainable from the site, where the order of the above-described steps may be altered. The subject devices include at least one site flow characterization element for determining the flow characteristics of a potential physiological sampling site and/or at least one sample type characterization element for determining whether the vasculature is arterial, venous or neither, i.e., an interstitial fluid sampling site. The subject methods and devices are particularly suited for use in the detection of physiological sampling sites in the fingers, arms, legs, earlobes, heels, feet, nose and toes. Also provided are kits that include the subject devices for use in practicing the subject methods.

DETAILED DESCRIPTION OF THE INVENTION

Methods and devices are provided for determining a suitable site for sampling physiological fluid. In the subject methods, a potentially suitable physiological sampling site is selected, the fluid flow of the site is characterized and the site is then determined to be suitable based on the whether the site has high or low flow. Suitability may also be determined based on the type of sample obtainable from the site, where the order of the above-described steps may be altered. The subject devices include at least one site flow characterization element for determining the flow characteristics of a potential physiological sampling site and/or at least one sample type characterization element for determining whether the vasculature is arterial, venous or neither, i.e., an interstitial fluid sampling site. The subject methods and devices are particularly suited for use in the detection of physiological sampling sites in the fingers, arms, legs, earlobes, heels, feet, nose and toes. Also provided are kits that include the subject devices for use in practicing the subject methods. In further describing the subject invention, the subject methods will be described first, followed by a review of the subject devices for use in practicing the subject methods.

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a vessel" includes a plurality of such vessels and reference to "the device" includes reference to one or more devices and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

As summarized above, the subject invention provides methods for determining a suitable site for sampling physiological fluid and in some embodiments also provides methods for piercing the skin at the suitable site and further determining the presence and/or concentration of at least one analyte in a sample collected from the site, usually automatically. The subject methods find use in the sampling of a wide variety of physiological fluids, where such physiological fluids include, but are not limited to, interstitial fluids, blood, blood fractions and constituents thereof, and the like. Where the determination of analyte concentration is employed, the subject methods find use in the determination of a wide variety of different analyte concentrations, where representative analytes include glucose, cholesterol, lactate, alcohol, and the like. In many embodiments, the subject methods are employed to determine the glucose concentration in physiological fluid.

The subject methods determine a suitable sampling site, where suitable sites may be located on various regions of the body, including, but not limited to, the fingers, arms, legs, earlobes, heels, feet, nose and toes. Where, for example, blood is the targeted physiological sample, a potential sampling site is characterized as suitable if the site has a high flow of arterial or venous blood. However, where interstitial fluid or the like is the target physiological sample, a potential sampling site is characterized as suitable if the site has no or substantially no or low amount of arterial or venous blood. Alternatively, the site may be determined to be unsuitable for sampling either blood or interstitial fluid.

Figure 1:
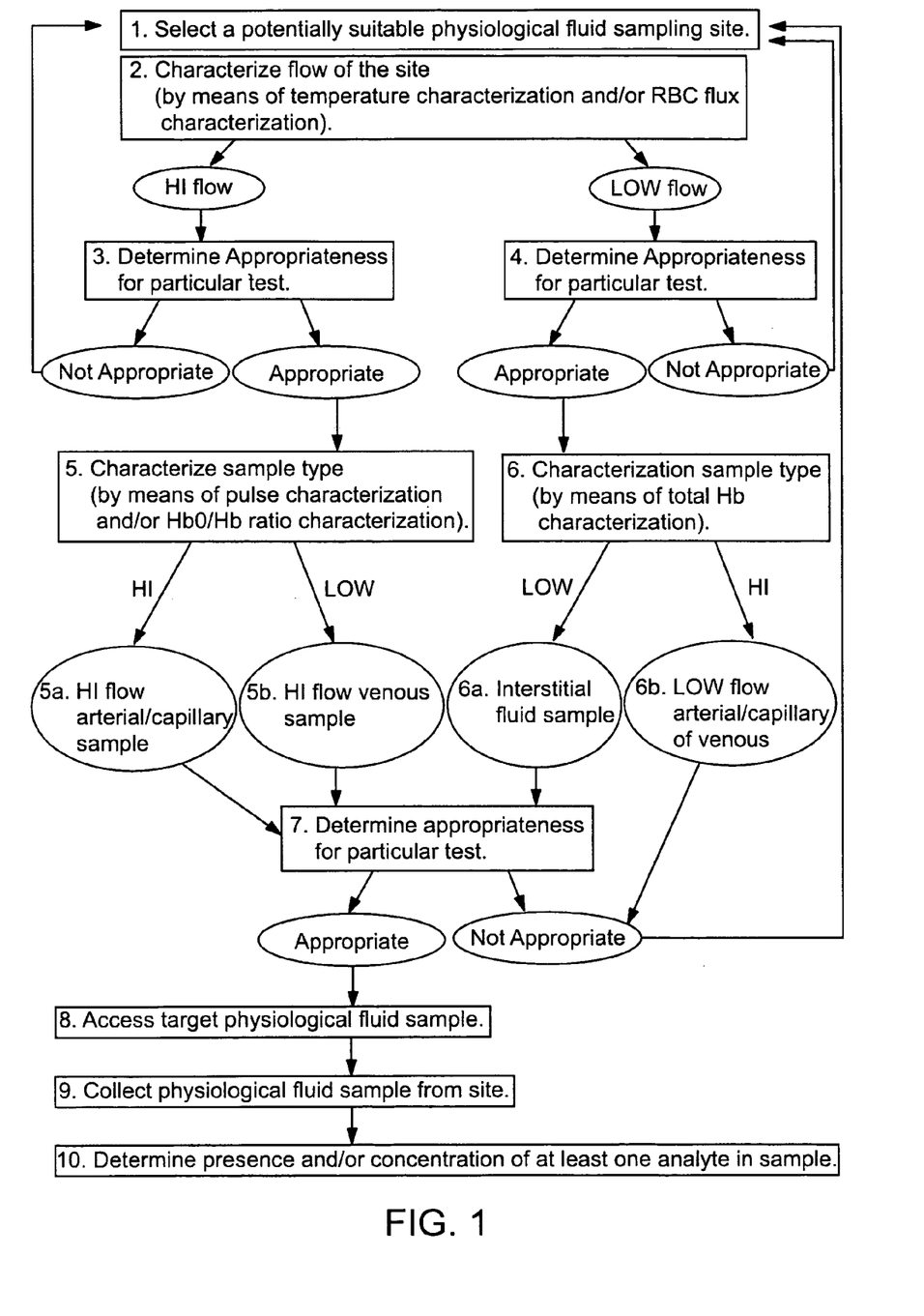
FIG. 1 shows a schematic block diagram representing the subject methods.

FIG. 1 provides a schematic block diagram representing the methods of the present invention. It will be apparent that the steps recited herein may be practiced in any order and certain steps may be subtracted or added, as deemed appropriate for a particular intended use. For example, it may be appropriate to only characterize the flow of the potential site or it may be appropriate to only characterize the type of sample obtainable from the site. Still further, it might be appropriate to characterize the type of sample obtainable from the site first, followed by a characterization of the flow, etc. The subject methods will be described herein as serial, i.e., performing site flow characterization first and/or performing sample type characterization second, where such a serial description is by way of example only and not limitation. It is to be understood, and will be apparent, that any sequence of steps or subtractions and/or additions of such steps is contemplated by this invention.

Turning now to the Figures, FIG. 1 is a flow chart of the subject methods used to determine a suitable sampling site. The first step in the subject methods is to select a potentially suitable physiological fluid sampling site (step 1). As described above, the potentially suitable site is typically on the fingers, arms, legs, earlobes, heels, feet, nose and toes, usually on the fingers or arms. Flow characterization is then performed, in other words, a determination of whether the site is a high flow site or a low flow site is made (step 2). The appropriateness of the site for a particular test is then determined (steps 3 and 4). If the site is found inappropriate, another potentially suitable site is then selected (return to step 1). If appropriate, sample type characterization may then be performed (steps 5 and 6). More specifically, a potential site is then characterized as having the ability to produce or express substantially arterial sample, substantially venous sample or neither, i.e., substantially interstitial fluid. The appropriateness of the sample type for a particular test is then determined (step 7). If the site is found inappropriate, another potentially suitable site is then selected (return to step 1). In certain embodiments, once the site is determined to be suitable for a particular testing protocol, the target physiological sample is accessed and collected from the site (steps 8 and 9). The presence and/or concentration of one or more analytes in the sample may also be determined by the subject methods, often times automatically (step 10).

I. Site Flow Characterization

As described above, the subject methods include the flow characterization of a potentially suitable sampling site. In other words, the flow or flow rate or velocity of the potential site is characterized, where a high flow rate will yield relatively larger sample volumes as compared to a low flow rate site. A variety of methods may be used to determine the flow characteristics of a potential site, where temperature determination and/or red blood cell ("RBC") characterization such as RBC flux, as will be described below, are of particular interest. Using temperature, for example, high temperature is associated with high flow and low temperature is associated with low flow. In the case of RBC characterization, e.g., RBC flux, a high RBC flux is associated with high flow and low RBC characterization, e.g., RBC flux, is associated with low flow. Each of these methods will now be described in greater detail.

A. Temperature Characterization

In many embodiments of the subject methods, flow characterization, i.e., characterizing the flow or flow rate or velocity of a potential site, is determined by measuring the temperature of a potential site, on the principle that higher fluid flow is associated with higher temperature than a relatively lower flow of fluid would be. Accordingly, the temperature of a site is determined, where such a temperature may include one or more measurements, e.g., a plurality of measurements may be made and a statistically relevant value (mean, median, etc.) may be determined. Regardless of the number of measurements made at a potential site, a temperature value or signal relating to the temperature is determined, where the temperature or value or signal associated therewith may then be compared to a predetermined value. For example, if a temperature were determined to be above a predetermined value typically ranging from about 30.5° C. to 35° C., usually from about 31° C. to 32° C., for example, the site would be determined to have a high flow. Alternatively, if the temperature were to fall below a predetermined value, such as below a range that is typically from about 29° C. to 30.5° C. and usually from about 29° C. to 30° C., the site would be determined to have a low flow. Alternatively, or in addition to the above method employing a predetermined value to which the measured value is compared, in those instances where the best available site is sought amongst a plurality of sites tested, i.e., the most appropriate site in relation to other sites tested, the temperature value may be compared to other sites' temperatures.

This temperature measurement method may be in place of, or in addition to, other flow characterization methods, e.g., red blood cell flux, as will be described below. In those embodiments where the temperature measurement is in addition to other flow characterization methods, the temperature measurement may be performed before, during or at the same time as the other method(s).

Typically, this temperature characterization occurs in about 0.5 to 180 seconds and more usually in about 0.75 to 60 seconds, but usually takes no more than about 10 seconds.

More specifically, a temperature sensor such as a thermocouple, e.g., a thermocouple associated with the subject devices as will be described below, measures the temperature of the sampling site. Such a measurement may be processed by a microprocessor working under the control of a software program. The measurement is made, communicated to the microprocessor and the microprocessor may perform all the steps, calculations and comparisons necessary to determine the flow characteristics of a site.

B. RBC Characterization

In place of, or in addition to, the above described temperature methods, the flow of a potential site may be characterized by determining the RBC character of the site, e.g., RBC flux of the site. In other words, a determination of a high RBC flux corresponds to high flow and a determination of a low RBC flux corresponds to low flow, as mentioned above.

To determine flow based on RBC characteristics, techniques based upon the frequencies of light or more particularly the change in the frequencies of light as the light encounters objects in its path such as RBCs, may be used. For example, techniques employing Doppler flowmetry methods may be employed, where Doppler flowmetry is well known in the art and includes the transmission and measurement of light, i.e., laser Doppler flowmetry (see for example Berardesca et al., *Bioengineering of the Skin: Cutaneous Blood Flow and Erythmea,* CRC Press, (1995)).

RBC characterization may be in addition to, or in place of, other site flow characterization methods. Where RBC characterization is in addition to other methods, the methods may be performed at the same or different times.

As mentioned, generally the subject RBC characterization methods measure the change in frequency of light waves, i.e., the change in frequency that light waves undergo when reflected by moving objects such as RBCs. Typically, skin is irradiated with coherent, single wavelength light which penetrates to a depth dependent on the wavelength of the light (the longer the wavelength, the deeper the penetration). A short distance away, light scattered back from the underlying tissue is detected by a broadband photodetector (the larger the distance between the source and detector, the deeper the tissue being observed). Light which has scattered back from immobile objects is the same frequency as the original illuminating beam. Light which is scattered back from moving objects, such as RBCs flowing in blood vessels, has a slightly shifted wavelength, with the shift dependant on the velocity of the moving objects. The shifted and unshifted light returning to the photodetector interacts in such a manner as to produce a low frequency (typically 0–20 kHz) oscillation or beat in the detected signal. The oscillating or AC component of the signal thus contains information about the velocity of flow of blood cells, while the average (DC) magnitude of the signal contains information about the total amount of light absorption and scattering in the tissue (which may correlate with the total amount of blood, both flowing and static, if the wavelength used is one where hemoglobin absorbs strongly).

Thus, a large average absorbance of light in ranges from about 450 nm to 600 nm or 850 nm to 950 nm indicates a high concentration of red blood cell-containing vessels, whether or not there was flow, where such a high concentration of red blood cell-containing vessels indicates a high concentration of arterioles, venuoles or capillaries. The AC signal is processed so that its power versus its frequency relationship is determined. The integral of this relationship between some lower and upper frequency bounds (e.g., 5 and 20 kHz) is determined, where the rate of flow increases as this integral increases. This integral is not completely linear with respect to flow, since higher frequencies are more sensitive to flow than lower ones. Therefore, outputs proportional to flow are employed, such as RBC flux. For example, formulas such as the formula $$RBC\ flux = \left( \int_{f_l}^{f_u} fP(f)\,df - N \right) / i^2$$

where f represents the shifted frequency, $f_l$ and $f_u$ represent the lower and upper cutoff frequencies, P(f) is the power at frequency f, N is a voltage offset and i is the mean photocurrent. RBC flux, as is known in the art (see for example Berardesca et al., *Bioengineering of the Skin: Cutaneous Blood Flow and Erythmea*, CRC Press, (1995)), may be used to generate outputs proportional to flow. The quantity or rather the magnitude of the RBC flux, as defined by the above-described formula, is substantially proportional to flow rate, where a high RBC flux corresponds to a high flow rate and a low RBC flux corresponds to a low RBC flux.

Accordingly, in the present invention, light at a wavelength in the range from about 400 nm to about 1200 nm, usually from about 450 nm to 800 nm is emitted from a light source such as a laser or the like and directed at the sample site, where such sources of light may be activated manually or automatically. The intensity of reflected light (the light reflected from red blood cells), and more specifically the change with time of the light, is measured and a value related to the character of the RBCs of the site, such as RBC flux, is determined. Such measurements may be fed into a microprocessor working under the control of a software program, where the microprocessor then determines the value related to the character of the RBCs of the site, such as RBC flux, which is proportional to the flow rate of a fluid in a vessel.

In one instance, the RBC characterization value, e.g., the RBC flux value or a statistically relevant value corresponding to the RBC flux value may be compared to a predetermined value, e.g., by means of a microprocessor. A comparison may then be made such that of the RBC value is above the predetermined value, the site is characterized as having a high flow rate and if the RBC value is below the predetermined value, the site is characterized as having a low flow rate. Alternatively, the best site (a highly appropriate site) amongst a plurality of potential sites tested may be determined by comparing RBC values of other tested sites.

Typically, RBC characterization is performed in about 1 to 180 seconds, usually in about 2 to 90 seconds and more usually in about 3 to 60 seconds.

II. Sample Type Characterization

As described, the subject methods include sample type characterization, where such methods determine whether a site is capable of expressing or producing substantially arterial sample, substantially venous sample or substantially interstitial fluid. More specifically, when used in conjunction with the above described methods for characterizing flow, the particular sample type obtainable from a potential site can be characterized in regards to flow rates and sample type. In other words, a potential sampling site can be characterized as (1) high flow rate, arterial/capillary, (5a of FIG. 1) (2) high flow rate, venous, (5b of FIG. 1), (3) low flow rate, arterial/capillary or venous, (6b of FIG. 1) or (4) low flow rate, interstitial fluid (6a of FIG. 1). As noted above, the sample type characterization may be in addition to, or in place of, flow characterization, where the order of these may be changed or altered.

A variety of methods may be used to characterize the sample type obtainable from a potential sampling site, where pulse characterization and hemoglobin characterization are of particular interest. For example, if a high flow site is characterized as having a high pulse and/or a high oxygenated hemoglobin/deoxygenated hemoglobin ratio (where herein HbO represents oxygenated hemoglobin and Hb represents deoxygenated hemoglobin and HbO/Hb represents the ratio thereof), it is determined to be a site having substantially high flowing arterial sample (5a of FIG. 1) and if a high flow site is characterized as having low pulse or low HbO/Hb ratio, it is determined to be a site having substantially high flowing venous sample (5b of FIG. 1). Furthermore, if a low flow site is characterized as having a high total hemoglobin level or value it is determined to be a site of low flow arterial, capillary or venous sample (6b of FIG. 1) and if a low flow site is characterized as having a low total hemoglobin level or value it is determined to be a site of interstitial fluid (6a of FIG. 1). Thus, the subject invention provides methods that enable an individual to select a sampling site according to the amount or volume and/or type of sample obtainable from the site.

Any convenient method may be used to characterize the pulse and/or hemoglobin values or levels of a potential site, where RBC characterizations and hemoglobin characterizations (total hemoglobin and HbO/Hb ratio) are of particular interest. Each of these methods will now be described in greater detail.

A. Pulse Characterization

As described above, once the flow of a site has been characterized, the determination of whether the pulse of such a site is relatively or substantially high or low will further enable characterization of the type of sample obtainable from the site. For example, if a site is characterized as having high flow, a high pulse characterization correlates to a substantially arterial/capillary site and a low pulse characterization correlates to a substantially venous site, a relatively lower or substantially no pulse site correlates to an interstitial fluid site.

In certain embodiments, pulse can be determined by determining the RBC characteristics of a site, e.g., RBC flux, as described above. The methods for determining RBC characteristics such as RBC flux have been described above and will not be repeated here. Once the RBC flux is determined, further characterizing pulsations (from the RBC flux) corresponding to cardiac pulse indicates whether the site is arterial or venous, based on the principle that an arterial/capillary site will have a greater pulse than a venous site. Cardiac pulsations are observed as oscillations with a frequency of typically between 60 and 100 pulses per minute in the RBC flux vs. time relationship, as described above (it will be apparent to one of skill in the art that certain clinical conditions may result in higher or lower frequencies). The pulsations result from flow surges in arteries and capillaries. Because of the resistance to flow of the capillaries, flow pulsations do not occur in veins. More specifically, if pulsations ranging from about 0.33 to about 3.3 Hz, usually from about 0.67 to 2.50 Hz and more usually from about 0.85 to 1.67 Hz are characterized at the site, the site is characterized as arterial. Alternatively, if pulsation in this frequency range is not detected or is very weak, the site is characterized as venous, where pulsations less than the arterial/capillary pulsation levels indicates a site devoid or substantially devoid of vasculature. Thus, if a site is determined to have a high RBC flux (high flow) and is also highly pulsatile, the site is characterized as arterial/capillary, i.e., high flow and arterial/capillary, rather than venous. If the RBC flux is determined to have low or substantially no pulsatile flow, the site may either be devoid of vasculature or may be venous, i.e., an interstitial fluid site or a high flow and venous site.

B. Hemoglobin Characterization

In other methods of the present invention, sample type characterization is determined by characterizing the hemoglobin character of the site, for example a characterization of the total hemoglobin of the site will enable a determination of whether the site is capable of expressing arterial/capillary or venous sample or interstitial fluid, based on the principle that a site having substantially interstitial fluid will have little or no hemoglobin. Also, as an arterial/capillary site will have a greater amount of HbO than a venous site, characterizing a site's HbO/Hb ratio will enable a determination of whether the site is capable of expressing substantially arterial/capillary sample or substantially venous sample.

Accordingly, methods to measure optical properties of the potential site are used to determine the hemoglobin characterization of the potential site. In other words, the absorbance, e.g., the light reflected from, or transmitted through, the potential site is detected and measured, i.e., an external portion of skin is irradiated with light (where light in this context does not necessarily refer to visible light, but may also include infrared light, etc.), and the absorbance of the light is detected, where such absorptions are indicative of hemoglobin characteristics of the site. In certain embodiments of the subject methods, the measured value is compared to a predetermined value to characterize the site. In other embodiments, it is compared to other hemoglobin values of other tested sites.

As described above, a site is irradiated with light and the light absorbed by the site, or rather the light reflected by or transmitted through the area of interest, is detected, where such detecting involves collecting the reflected or transmitted light or a statistically relevant value thereof, for example by at least one light detector of an optics element, and processing the detected data to determine the hemoglobin character of the site. For example, the detected light or a respective signal may be transferred to a microprocessor for further processing, where the microprocessor works under the control of a software program. In other words, the program code in the software program instructs the microprocessor to carry out all the steps necessary to accomplish the particular task. Regardless of whether performed manually or automatically, the amount, magnitude or quantity of the reflected or transmitted light or a signal or relevant statistical value thereof may be compared to a predetermined value. For example, if the signal were to be above a predetermined value, the site might be determined to have a high total hemoglobin level or high HbO/Hb ratio. Alternatively, if the signal were to fall below a predetermined value, the site might be determined to have a substantially low hemoglobin level or low HbO/Hb ratio. Alternatively, or in addition to, the above method employing a predetermined value to which the measured value is compared, in those instances where the best available site is sought, i.e., the most appropriate site in relation to other sites tested, the measured value or statistically relevant value thereof may be compared to measured values of other tested sites. Typically, this optical irradiation and detection takes about 0.1 to 180 seconds and more usually about 0.1 to 60 seconds, and more typically about 0.1 to 20 seconds.

Thus, in practice, light from at least one light source, i.e., an optics element, e.g., at least one LED, laser emitting diode, light emitter, bispectral emitter, dual spectral emitter, photoemitter, photodiode, a semiconductor die or the like at a wavelength in the range from about 400 to 1200 nm, irradiates the site, where in some embodiments more than one wavelength is used from the same or different light sources, where the different wavelengths may irradiate the site at the same or different times. Usually, the site will be irradiated for about 0.1 to 180 seconds, typically about 0.1 to 60 seconds and more typically about 0.1 to 20 seconds and then the absorbed light will be detected by a suitable detector such as at least one of the following: a photodiode, a photoelectric receiver, a photodetector, a semiconductor die, or the like. The detected signal is then related to hemoglobin concentration, i.e., total hemoglobin or a component or suitable ratio thereof. In certain embodiments, the detected light is then communicated to a suitable microprocessor for further processing such as computational processing and the like.

By way of background, generally when the skin is illuminated by light, if the light were to enter the skin, reflect off the collagen at the bottom of the dermis and re-emerge from the skin without absorption by an chromophores, (e.g., melanin or hemoglobin), the signal (remittance) detected and thus generated by the photodetector could be defined as $R_c$. When chromophores in the epidermis (melanin) and the dermis (hemoglobin) intervene, the reflectance is attenuated, giving a signal defined as $R_{tot}$. Thus, an equation representative of the signal received is defined as:

$$R_{tot} = T_m^2 \cdot T_{HbO}^2 \cdot T_{Hb}^2 \cdot R_c \quad (1)$$

Where:

$T_m$ represents the fraction of light allowed to pass through the epidermis without being absorbed by melanin.

$T_{HbO}$ represents the fraction of light allowed to pass through the dermis to the collagen layer without being absorbed by oxyhemoglobin.

$T_{Hb}$ represents the fraction of light allowed to pass through the dermis to the collagen layer without being absorbed by deoxyhemoglobin.

Thus, the Beers-Lambert formulation (i.e., the equation representing the principle that the degree of absorption of light varies exponentially with the thickness of the layer of the absorbing medium, its molar concentration and extinction coefficient) of equation 1 above is:

$$A = -\ln(R_{tot}/R_c) = 2\{I_E[M]\epsilon_M + I_D[HbO]\epsilon_{HbO} + I_D[Hb]\epsilon_{Hb}\} \quad (2)$$

Where:

A represents the absorbance at the site.

I represents the effective path length of the zone represented by the subscript.

E, D represents dermis and epidermis, respectively.

[ ] represents molar concentration.

M, HbO, Hb represent melanin, oxyhemoglobin and deoxyhemoglobin, respectively.

$\epsilon$ represents the molar extinction coefficient (unique for each wavelength).

Thus, it will be apparent that if blood is substantially prevented from entering a potential sampling site while an optical reading is taking place, the absorbance in equation 2 above is a function only of the melanin absorbance such that:

$$A = -\ln(R_{tot}/R_c) = 2I_E[M]\epsilon_M \text{ or} \quad (3)$$

$$\ln(R_{tot}) = \ln(R_c) - 2I_E[M]\epsilon_M = C, \quad (4)$$

where C represents the melanin absorbance or background signal. Thus, the light absorbance resulting from hemoglobin can be represented by:

$$\ln(R_{tot}) = C - 2\{I_D[HbO]\epsilon_{HbO} + I_D[Hb]\epsilon_{Hb}\} \quad (5)$$

Again, $R_{tot}$ is the signal received by the photodetector. Thus, to obtain the background signal, a site having substantially no blood flow, i.e., a site where pressure is applied has been applied thereto to substantially prevent blood flow to the site, the absorbance due to hemoglobin only can be determined by first determining C from equation 4 above, where $R_{tot}$ is the signal obtained from the first occluded optical measurement, and then solving for hemoglobin terms in equation 5 using $R_{tot}$ from the second optical measurement where blood was not prevented from entering the site.

As such, since the molar extinction coefficients for both oxy and deoxygenated hemoglobin are known for all wavelengths in the visible and near infrared range (see for example O. W. Van Assendelft, *Spectrophotometry of Hemoglobin Derivatives*, Charles Thomas, pub., 1970), oxy and deoxygenated hemoglobin can both be determined by using more than one wavelength. Accordingly:

$$I_D[HbO] = (C_1 - \ln(R_{tot})_1 - (C_2 - \ln(R_{tot})_2)(\epsilon_{Hb1}/\epsilon_{Hb2})/(\epsilon_{HbO1}/\epsilon_{Hb2}) \quad (6)$$

$$I_D[HbO] = (C_1 - \ln(R_{tot})_1 - I_D[HbO](\epsilon_{HbO1}/\epsilon_{Hb1}) \quad (7)$$

Subscripts 1 and 2 represent wavelengths 1 and 2. In using the subject methods to characterize the hemoglobin of a potential site, the wavelengths are typically chosen so as to have very different extinction coefficients, i.e., wavelengths are usually chosen to make equations 6 and 7 as orthogonal as possible.

Accordingly, the first step in the subject methods to the characterize hemoglobin of a site is to determine the background signal at the site. By background is meant the absorbance of the site not related to hemoglobin, for example the absorbance related to melanin and the like. As such, light of two different wavelengths irradiates a potential site and the background signal is detected.

More specifically, wavelengths of light are chosen such that the molar extinction coefficient deltas of the oxy and deoxygenated hemoglobins are different for the different wavelengths chosen, i.e., as one molar extinction coefficient goes up the other molar extinction coefficient goes down, where such molar extinction coefficient deltas of oxy and deoxygenated hemoglobin are known in the art. Thus, to determine the background signal, the potential site is temporarily substantially occluded or rather blood is temporarily substantially stopped or prevented from entering the site, for example by pressing against the site, e.g., by pressing or applying pressure by the aperture of the device described below onto the surface of the skin with enough force as to substantially stop blood flow to the site. In this way, the site is substantially devoid of any hemoglobin and thus any absorbance will be attributed to background or the absorbance of various chromophores at the site such as melanin. Once signal is detected from such an occluded potential site, the background value is then determined based upon the above described equations, typically automatically. More specifically, the signal detected by such a background determining method is communicated to a microprocessor, where such a microprocessor computes the background level or value of the site.

Following the background reading from the occluded site, a second reading at the site is taken. More specifically, light of two different wavelengths irradiates the site, where such wavelengths are chosen such that there is a large and opposite delta of the extinction coefficients of the two wavelengths. Once the signals from the two wavelengths are detected, the various components of hemoglobin can be determined from the above described equations, i.e., equations 6 and 7, typically automatically by a microprocessor as described above. In other words, oxygenated hemoglobin, deoxygenated hemoglobin and total hemoglobin (the sum of the oxygenated and deoxygenated hemoglobin components) can be determined, where such a determination can then be compared to a predetermined or cut-off value such that a total hemoglobin value and/or a hemoglobin ratio value, i.e., a ratio value defined by HbO/Hb, above the predetermined value is designated as a high hemoglobin value and a hemoglobin value below the predetermined value is designated as a low hemoglobin value. As noted above, alternatively, the values may be compared to other tested sites such that the best site among those tested is chosen.

Referring again to FIG. 1, if a site has been characterized as having low flow, a further determination regarding total hemoglobin level will enable characterization of the site as having substantial vasculature (high total Hb) (6b of FIG. 1) or substantially devoid of vasculature, i.e., interstitial fluid (low total Hb) (6a of FIG. 1). Once vasculature versus interstitial fluid or substantially no vasculature is determined, the site is then further characterized as being appropriate or not for a particular test (7 of FIG. 1). In other words, if the particular test requires interstitial fluid, the potential sampling site will be determined to be appropriate if the total hemoglobin site is found to be low, thus determined to be capable of expressing interstitial fluid. Site appropriateness will be described in greater detail below.

If the site has been characterized as having high flow according to the above described methods, a HbO/Hb ratio can then be determined, where such a ratio enables characterization of a site as either high flow and arterial/capillary (5a of FIG. 1) or high flow and venous (5b of FIG. 1). In other words, a site having a relatively or substantially high concentration of HbO to Hb is indicative of an arterial/capillary site and a site having a relatively or substantially low concentration of HbO to Hb is indicative of a venous site. Specifically, a hemoglobin ratio is determined based upon the above described equations, typically automatically by a microprocessor, where such a determination can then be compared to a predetermined or cut-off value such that a ratio value above the predetermined value is designated as a high ratio value and a ratio value below the predetermined value is designated as a low ratio value. As noted above, alternatively, the values may be compared to other tested sites such that the best site among those tested is chosen. Once arterial/capillary versus venous is determined, the site is then further characterized as being appropriate or not for a particular test (7 of FIG. 1). In other words, if the particular test requires arterial/capillary sample, the potential sampling site will be determined to be appropriate if the HbO/Hb ratio is found to be high, thus it is determined to be capable of expressing substantially arterial/capillary sample, particularly high flow arterial/capillary sample. However, if the particular test requires venous sample, the potential sampling site will be determined to be appropriate if the HbO/Hb ratio is found to be low, thus it is determined to be capable of expressing substantially venous sample, particularly high flow venous sample. Site appropriateness will be described in greater detail below.

As described in detail above, in practicing the subject methods for hemoglobin characterization, whether HbO, Hb or total hemoglobin, light sources such as LED's, laser diodes, etc., irradiate a site, where the light sources irradiate the site with at least two different wavelengths, each of which ranges from about 400 to 1200 nm. A photodetector detects the absorbed light and the amount of each hemoglobin component can then be determined based on the specific absorbances of the wavelengths of interest, where such absorbances are then related to the particular hemoglobin component. More particularly, a device having the above described optical components, such as a device described in detail below, may be used to practice the subject methods. As such, the device also is typically operatively coupled to a microprocessor working under the control of a software program such that the microprocessor is capable of performing all of the steps and functions necessary to characterize the hemoglobin of the site and also determine the appropriateness of the site for a particular test, for example the microprocessor is capable of performing all of the computations and/or comparisons necessary to determine oxygenated, deoxygenated and/or total hemoglobin values. As mentioned above, the above-described methods, the total hemoglobin and/or HbO/Hb ratio may be compared to a predetermined value or may be used as a comparison against other values from other tested sites to determine the best site amongst a plurality of sites testes. Additionally, the optical determination described herein may be in addition to, or instead of, other sample type characterization methods.

In certain other embodiments of the subject methods, hemoglobin characterization may be derived according to the methods described below, where the below described methods are of particular use where the path lengths and melanin concentrations are substantially constant from site to site and it is desirable to characterize the total hemoglobin concentration of a potential site.

Again by way of background, at a number of wavelengths such as 506.5, 522, 548,5, 586 and 815, HbO and Hb have the same molar extinction coefficients. If $R_{tot}$ is measured at any of the wavelengths where HbO and Hb have the same molar extinction coefficients, the magnitude of $R_{tot}$ will increase or decrease as total hemoglobin decreases or increases, respectively, based on the principle that C is substantially constant from site to site. Thus, in certain embodiments, total hemoglobin can be determined using the following equation:

$$\ln(R_{tot}) = C - 2\{I_D[HbO](\varepsilon_{HbO} = \varepsilon_{Hb}) + I_D[Hb](\varepsilon_{HbO} = \varepsilon_{Hb})\} \quad (7)$$
$$= C - 2 I_D(\varepsilon_{HbO} = \varepsilon_{Hb})([HbO] + [Hb])$$

Thus, for this particular embodiment, light of one wavelength irradiates a site, where such wavelength is chosen such that HbO and Hb have the same molar extinction coefficient. The absorbance or signal is then detected from the site and the total hemoglobin at the site is determined based upon the above described equation, where oftentimes the total hemoglobin concentration is determined automatically by a microprocessor. More particularly, light from a light source such as an LED, laser diode, or the like irradiates a site with light of one wavelength, where the extinction coefficients of both HBO and Hb are the same. The absorbance or signal of the site is detected by a suitable photodetector or the like, where such absorbance is related to the total hemoglobin level of the site. Once total hemoglobin has been determined, the site is then further characterized as being appropriate or not for a particular test. In other words, for example, if the particular test requires interstitial fluid, the potential sampling site will be determined to be appropriate if the total hemoglobin site is found to be low, and the site is thus determined to be capable of expressing interstitial fluid. Site appropriateness will be described in greater detail below.

In yet another embodiment of the subject methods, hemoglobin characterization may be derived according to the methods described below, where the below described methods are of particular use where the path lengths and melanin concentrations are substantially constant from site to site and it is desirable to characterize a hemoglobin ratio of a potential site, e.g., HbO/Hb.

In this particular embodiment, two wavelengths are chosen to irradiate a site, where, at each wavelength, the two hemoglobin species have substantially different extinction coefficients, i.e., oxygenated hemoglobin and deoxygenated hemoglobin have different extinction coefficients. For example, suitable wavelengths where HbO and Hb have substantially different extinction coefficients include, but are not limited to, 431, 415, 555, 700 and 940 nm. That is, a first wavelength and a second wavelength are chosen, where each wavelength may be selected from the above described set of wavelengths so that HbO and Hb will have substantially different wavelength coefficients. The extinction coefficients at such suitable wavelength pairs have opposite deltas between the two wavelengths, i.e., as one increases between the first and second wavelengths, the other decreases between the first and second wavelengths. As such, the difference in $\ln(R_{tot})$ between the two wavelengths will increase as one hemoglobin component increases and will decrease as the other hemoglobin component deceases. In other words, for example, for each suitable chosen wavelength pair, as HbO increases, the difference in $\ln(R_{tot})$ between the two wavelengths will increase and as Hb decreases, the difference in $\ln(R_{tot})$ between the two wavelengths will decrease.

More specifically, from equation 5 above, modified for two wavelengths:

$$\ln(R_{tot})_1 = C_1 - 2\{I_D[HbO]\epsilon_{HbO1} + I_D[Hb]\epsilon_{Hb1}\}$$

$$\ln(R_{tot})_2 = C_2 - 2\{I_D[HbO]\epsilon_{HbO2} + I_D[Hb]\epsilon_{Hb2}\}$$

$$\ln(R_{tot})_1 - \ln(R_{tot})_2 = C_1 - C_2 - 2I_D\{[HbO](\epsilon_{HbO1} - \epsilon_{HbO2}) + [Hb](\epsilon_{Hb1} - \epsilon_{Hb2})\} \quad (8)$$

Thus, if $(\epsilon HbO_1 - \epsilon HbO_2) > 0$ and $(\epsilon Hb_1 - \epsilon Hb_2) < 0$, then $\ln(Rtot)_1 - \ln(Rtot)_2$ increases as [HbO] increases or [Hb] decreases. For example, if the extinction coefficient of HbO is greater at wavelength 1 than wavelength 2, and Hb has an extinction coefficient that is less at wavelength 1 than wavelength 2, then as the difference between the signals (i.e., the difference between wavelength 1–wavelength 2) increases, the ratio of HbO to Hb will increase. In many embodiments, this method of characterizing total hemoglobin concentration is performed first, such that this method of characterizing HbO/Hb ratios is performed on a site having a high hemoglobin concentration. In other words, because the total hemoglobin concentration affects the difference calculation, characterizing HbO/Hb ratios should be performed on a site having a substantially high total hemoglobin concentration.

Specifically, a potential site is illuminated with two wavelengths from two light sources, where such light sources may include one or more LED, one or more laser diode, etc. The wavelengths are chosen such that the molar extinction coefficient deltas of HbO and Hb are different between the two wavelengths, i.e., as one goes up the other goes down, as described above. At least one photodetector detects the signal from the site, i.e., the absorbance of the light, where such signal is related to an HbO/Hb ratio, according to the above described equations. The site is then further characterized as being appropriate or not for a particular test. Site appropriateness will be described in greater detail below.

III. Determine the Appropriateness of a Site for a Particular Test

Figure 2:
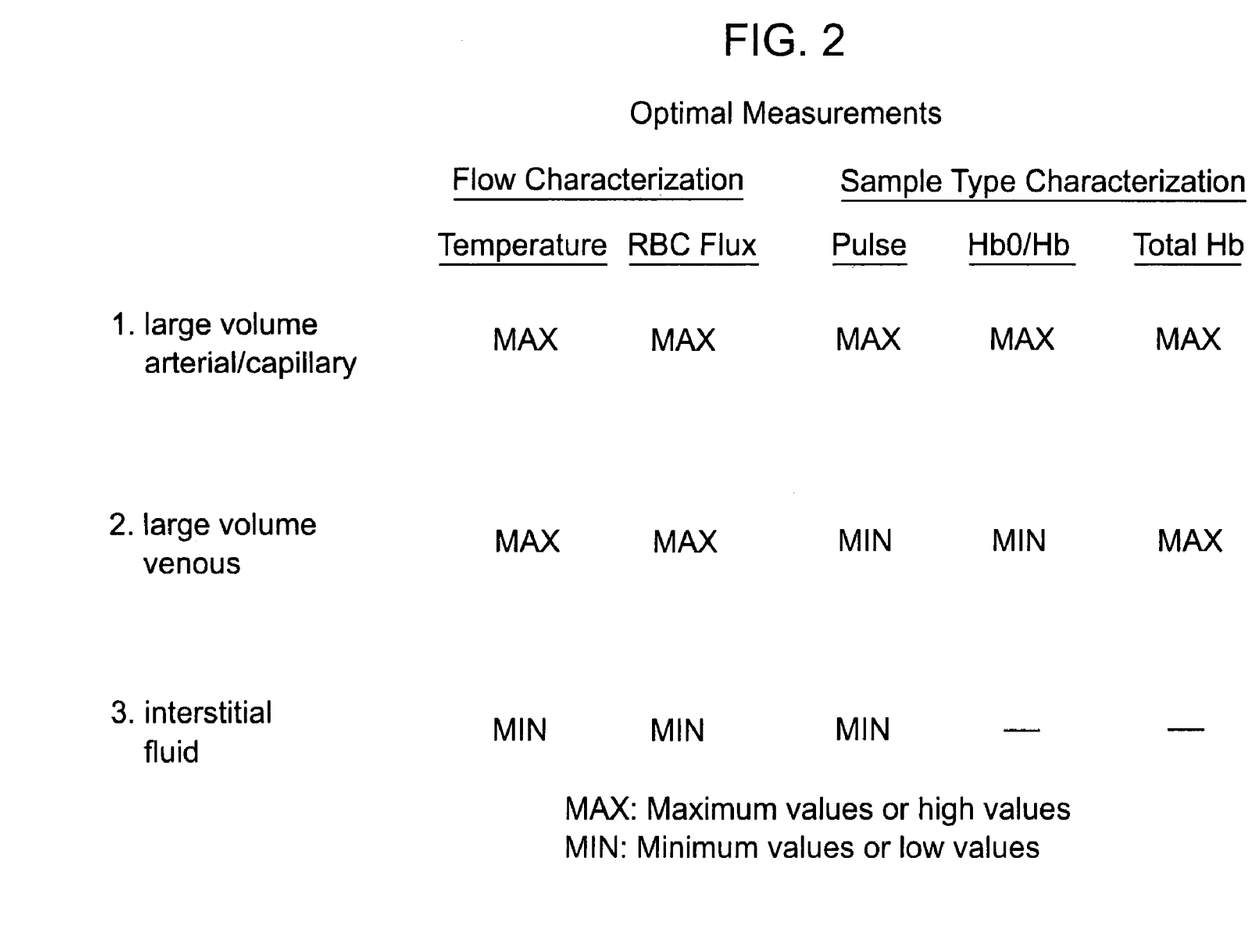
FIG. 2 shows a graph of optimal measurements of the subject invention correlated to specific sample type obtainable.

As mentioned above, the appropriateness of a site for a particular test is determined by the subject methods. Referring now to steps 3, 4 and 7 of FIG. 1, as described above, once a site is characterized by flow and/or sample type, its appropriateness in regards to the particular test to be performed is evaluated. Such appropriateness is best described in reference to FIG. 2, which shows certain sample test parameters and their correlation to particular samples obtainable from a site. For example, certain tests require a minimum sample volume. Thus, a site which is characterized as being capable of producing or expressing a greater volume of sample (a site having higher flow rate) would be preferable to a site not so capable, e.g., high flow of arterial/capillary and/or venous would be more appropriate versus a low flow site of arterial/capillary and/or venous, unless the particular test required interstitial fluid as opposed to arterial/capillary or venous blood. As such, test results meeting the requirements of such samples would be determined to be appropriate.

Also, certain tests such as glucose tests calibrated to whole blood may require a certain type of sample such as blood, blood constituents or the like as the appropriate fluid sample and as such a site will be determined appropriate for such a test if the site is characterized as arterial/capillary and/or venous and likewise inappropriate if it is characterized as having interstitial fluid. However, certain other tests such as glucose tests calibrated to interstitial fluid may, accordingly, require interstitial fluid as the appropriate fluid sample and as such a site will be determined appropriate if the site is characterized as having interstitial fluid and likewise inappropriate if it does not.

Furthermore, some tests may require arterial blood instead of venous blood, or vice versa, and as such will be determined appropriate if the site is characterized as having the requisite arterial or venous blood and inappropriate if it does not. In other words, a test that requires arterial/capillary and/or venous blood would thus correlate to a high flow arterial/capillary and/or high flow venous site. A test that requires interstitial fluid would thus correlate to a low flow interstitial fluid site. A site characterized as low flow arterial/capillary or venous site would thus likely not be appropriate for any test.

As described above, in many embodiments of the subject methods, appropriateness of a site for a particular test is typically accomplished automatically by a microprocessor, where the microprocessor works under the control of a software program and includes all the code necessary for it to carry out the steps required to determine if a site is appropriate for a particular test.

IV. Skin Piercing

Once an appropriate site has been determined, sample is then accessed and collected (steps 8 and 9 of FIG. 1). Typically, sample is collected from the dermis and epidermis. In certain methods, the sampling site may be stimulated to increase the volume and/or rate of sample produced or expressed at the sampling site.

Accordingly, in some embodiments, at least one skin-piercing element is inserted into the skin of a patient or user of the subject invention to access physiological fluid. Depending on the type of physiological sample to be obtained, the at least one skin-piercing element may penetrate to a particular skin layer, such as the dermis and epidermis layers. Typically, the at least one skin-piercing element is inserted into the skin for about 0.0001 to 60 seconds, usually about 0.0005 to 30 seconds and more usually from about 0.001 to 15 seconds so as to ensure an adequate sampling volume of the targeted physiological fluid is obtained.

The at least one skin-piercing element may be activated manually by the user by releasing an actuating element associated with the at least one skin-piercing element, e.g., by depressing a button or the like on a device which activates the spring-loaded element towards the skin, or may be automatically activated to pierce the skin, for example triggered automatically when a suitable sampling site is located.

In certain embodiments of the subject methods, the at least one skin-piercing element, or one or more elements operatively associated therewith, stimulates the site to produce or express a greater volume and/or rate of the physiological fluid desired of the physiological fluid desired, i.e., increases the rate of expression of physiological fluid. For example a fluid enhancing element, e.g., an ultrasonic element or the like, may be used to create vibrations at the site during fluid access and collection, where such vibrations stimulate fluid expression. In certain embodiments, the fluid enhancing means may include, in addition to or in place of other fluid stimulating elements, a temperature element to increase the temperature of the site to stimulate fluid expression. The fluid enhancing element may be operatively associated with the at least one skin-piercing element such that the at least one skin-piercing element stimulates fluid expression itself while it accesses the fluid from the site. In any event, in those embodiments employing an ultrasonic element to stimulate sample expression from a site, such an ultrasonic element typically vibrates at a frequency in the range from about 10 to 1000 Hz, where such vibrations stimulate the expression of physiological fluid, e.g., increase the volume and/or rate of sample production.

V. Analyte Concentration Determination

Many embodiments of the subject methods also include determining the concentration of at least one analyte in the physiological sample (step 10 of FIG. 1). As such, once a suitable sampling site is found and sample is accesses and collected therefrom, the concentration of at least one analyte of the sample may be determined using any appropriate analyte concentration determination method, as are known in the art.

In certain embodiments of the subject methods, the sample is then transferred to a standard analyte concentration determination reagent test strip, e.g., a glucose test strip or the like, which is in communication with the device, where oftentimes the test strip may be directly integrated into the device. In those embodiments where the test strip is directly integrated into the device, the test strip may be loaded directly into the device before, during or after the physiological sample is extracted, and in many instances may be manufactured with the test strip already integrated with the device.

Once sample is transferred to a test strip, i.e., delivered to the reaction area of the test strip, the concentration of at least one analyte of interest is determined. Sample may be transferred to a test strip by a variety of mechanisms, where such mechanisms include, but are not limited to, vacuum, capillary forces and the like. As will be apparent to one of skill in the art, a variety of analyte determination methods may be employed, e.g., electrochemical and calorimetric, where both methods will be described below.

For an electrochemical analyte concentration determination assay, an electrochemical measurement is made using reference and working electrodes, as is known in the art. The electrochemical measurement that is made may vary depending on the particular nature of the assay and the device with which the electrochemical test strip is employed, e.g., depending on whether the assay is coulometric, amperometric or potentiometric. Generally, the electrochemical measurement will measure charge (coulometric), current (amperometric) or potential (potentiometric), usually over a given period of time following sample introduction into the reaction area. Methods for making the above described electrochemical measurement are further described in U.S. Pat. Nos. 4,224,125; 4,545,382; and 5,266,179; as well as WO 97/18465; WO 99/49307; the disclosures of which are herein incorporated by reference. Regardless of the type of measurement, an electrochemical measurement or signal is made in the reaction zone of the test strip.

Following detection of the electrochemical measurement or signal generated in the reaction zone as described above, the amount of the analyte present in the sample introduced into the reaction zone is then determined by relating the electrochemical signal to the amount of analyte in the sample.

Generally, for colorimetric assays, the sample is allowed to react with a reagent system, e.g., members of a signal producing system, to produce a detectable product that is present in an amount proportional to the initial amount present in the sample. In one such system, e.g., in a system used to determine the presence and or concentration of glucose in a physiological sample, the signal producing system is an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. The amount of detectable product, i.e., signal produced by the signal producing system, is then determined and related to the amount of analyte in the initial sample. Of course, any type of colorimetric assay, i.e., various calorimetric chemistries, may be used with the present invention.

In many embodiments, the above described characterization and relation processes are performed by an automated device, e.g., a meter, as is well known in the relevant art. Representative meters for automatically practicing these steps are further described in copending U.S. application Ser. Nos. 09/333,793; 09/497,304; 09/497,269; 09/736,788 and 09/746,116, and U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference.

Devices

As summarized above, the invention provides devices for determining a suitable site for sampling physiological fluid, by way of a site flow characterization element and/or a sample type characterization element. The devices may also include at least one skin-piercing element for piercing the skin at the appropriate sampling site and/or include an operatively associated means for determining the presence and/or concentration of at least one analyte in a physiological sample extracted or expressed from the appropriate sampling site. The subject devices find use in the location of suitable physiological fluid sampling sites on various areas of the body, including, but not limited to, the fingers, arms, legs, earlobes, heels, feet, nose and toes. Furthermore, the subject devices find use in the location and collection of a wide variety of physiological samples, where such samples include, but are not limited to, interstitial fluids, blood, blood fractions and constituents thereof, and the like.

As described above, the subject invention includes at least one site flow characterization element and/or at least one sample type characterization element, where one or both types of the elements may be integrated into a housing or may otherwise be a single unit, i.e., an integrated device, usually with at least one skin piercing element and/or test strip. The unit, i.e., the housing, may be manufactured from a wide variety of materials including, but not limited to, polystyrene, polypropylene, polyethylene, polyacryonitrile, polycarbonate, and the like. The unit may be re-usable or single use.

The housing is intended to be easily held by the user, i.e., a hand-held device, and as such is sufficiently compact to enable portability and ease-of-use. Accordingly, the housing may take a number of different shapes, as long as the shape enables the functionability of the device, e.g., facilitates portability and grasping by the user and positioning on an appropriate sampling site area, such as a surface area of the skin. For example, the shape may be substantially irregular or may assume a substantially regular shape such as a parallelogram, rhombus, circle, oval and the like. Regardless of the shape, the unit and associated elements typically have a length in the range from about 1 to 20 inches, usually in the range from about 2 to 15 inches and more usually in the range from about 3 to 10 inches. The width of the unit is usually in the range from about 0.1 to 10 inches, usually in the range from about 0.2 to 5 inches and more usually in the range from about 0.5 to 3 inches. The height is usually in the range from about 0.1 to 10 inches, usually in the range from about 0.2 to 5 inches and more usually in the range from about 0.5 to 3 inches. The weight of the subject device is usually in the range from about 0.02 to 10 pounds and more usually in the range from about 0.04 to 5 pounds, but in most cases is less than about 2 pounds. The proximal end of the device, i.e., the end of the device which is in close proximity to or in direct contact with the skin when in use, typically includes a proximal orifice, where such an orifice usually has a diameter less than about 5 millimeters, and is in the range from about 1 to 4 millimeters, and more usually in the range from about 1 to 2 millimeters.

Typically, the visible surface of the unit will include a display or screen on which messages, instructions, error warnings, and most importantly, results, i.e., whether a site is suitable and/or the concentration of an analyte, may be displayed by means such as liquid crystal displays, as are known in the art. Such information may be conveyed by alphanumeric digits or units or pictorial icons. In certain embodiments, an audio means may also be present in or on the device for audibly conveying information to the user. Additionally, the subject device may include a power switch for manually activating the device.

I. Site Flow Element

As described above, in certain embodiments of the subject invention, the housing includes at least one site flow characterization element which characterizes the flow of a potential site, i.e., the flow rate or velocity of the site. A wide variety of elements or components may be employed to determine the flow characterizations of a particular sampling site, where particular embodiments of interest will now be described.

A. Temperature Characterization Element

In certain embodiments, the flow characterization element includes an element capable of characterizing the temperature of a potential site. For example, a temperature element or sensor such as a thermocouple or the like may be employed, where such thermocouples are known in the art. Such a temperature element may be in place of or in addition to, other elements used to characterize the flow of a site, such as the RBC characterization element described below, where one or more site characterization elements are capable of being activated at the same or different times, e.g., a temperature element is capable of being activated at the same or different time as a light detecting element, etc.

The temperature element of the present invention is one which is capable of measuring the temperature of the site, where such a temperature is an indication of the flow character of the site. In other words, the temperature of the skin increases as blood flow increases due to factors such as the velocity of the flow of fluid at the site.

Accordingly, the temperature sensor is capable of measuring infrared radiation or temperatures in the range from about 0 to 100° C., usually from about 10 to 75° C. and more usually from about 10 to 50° C. Typically, the temperature element will be positioned in close proximity to the proximal aperture of the device or housing; however, other positions may be employed as well depending upon the configuration of the device, the particular temperature sensor used and the specific body area to be tested.

B. RBC Characterization Element

In other embodiments, the flow characterization element is an element capable of characterizing the RBCs of the site, e.g., RBC flux characterization. RBC characterization elements may be in addition to, or in place of, other flow characterization elements, as described herein. Where the RBC characterization element is in addition to other elements, the elements may be capable of being activated at the same or at different times.

Typically, an element configured to perform RBC characterization, e.g., RBC flux determination as described above, usually includes at least one light source capable of emitting light, usually coherent, single wavelength light, at a wavelength ranging from about 400 to 1200 nm, usually from about 450 to 800 nm such as a laser as is commonly known in the art, and a sensor or detector, typically a broadband sensor or detector, for detecting the intensity of light reflected from the RBCs. The at least one light source may thus include one or more: light emitting diode (LED), laser diode, light emitter, bispectral emitter, dual spectral emitter, photoemitter, photodiode, semiconductor die, or the like, and the detector may include one or more: photodiode, photoelectric receiver, photodetector such as a broadband photodetector, semiconductor die, or the like.

Examples of commercially available elements capable of RBC characterization or RBC flux characterization, e.g., Doppler flowmeters, adaptable for use with the present invention include, but are not limited to, flowmeter models LD-5000 and LD-6000 manufactured by Medpacific of Seattle, Wash.; flowmeter models PF1, and models PF2 and PF3 manufactured by Perimed of Stockholm, Sweden. The RBC characterization element may be operatively associated with a microprocessor under the control of a software program that is capable of processing signal from the site and determining the RBC character, e.g., RBC flux, or a statistically relevant value thereof, of the site based upon the measured intensities of reflected light and may also perform the steps necessary to compare such a RBC characterization value or measurement such as RBC flux value to a predetermined value or to RBC characterization values of various tested sites.

II. Sample Type Characterization Element

As mentioned above, the subject devices may also includes one or more sample type characterization element, where such an element is capable of characterizing a site as either primarily or generally (1) arterial/capillary, (2) venous or (3) interstitial fluid, and more specifically is capable of characterizing the type of sample at a site as either primarily or generally arterial/capillary, venous or interstitial fluid. A variety of elements may be used to characterize the type of sample at a site. For example, elements include those capable of characterizing the pulse of a site and/or characterizing the Hb of the site, as will now be described in grater detail.

A. Pulse Characterization Element

The pulse characterization element is an element capable of characterizing the pulse of a site. Pulse characterization may be in addition to, or in place of, other sample type characterization elements, as described herein. Where the pulse characterization element is in addition to other elements, the elements may be capable of being activated at the same or at different times.

Typically, an element configured to perform pulse characterization usually includes at least one light source capable of emitting light, usually coherent, single wavelength light at a wavelength from about 400 to 1200 nm, usually from about 450 to 800 nm such as a laser as is commonly known in the art, and a sensor, typically a broadband sensor or detector for detecting the intensity of light reflected from the RBCs. The light source may include one or more: light emitting diode (LED), a laser diode, a light emitter, a bispectral emitter, a dual spectral emitter, a photoemitter, a photodiode, a semiconductor die, or the like, and the detector may include a photodiode, a photoelectric receiver, a photodetector such as a broadband photodetector, a semiconductor die, or the like.

The light source and detector may the same as or in addition to the above described elements used for RBC characterization. Examples of commercially available pulse characterization elements, e.g., Doppler flowmeters, adaptable for use with the present invention to determine flow characterization include, but are not limited to, flowmeter models LD-5000 and LD-6000 manufactured by Medpacific of Seattle, Wash.; flowmeter models PF1, and models PF2 and PF3 manufactured by Perimed of Stockholm, Sweden.

The pulse characterization element may be operatively may be associated with a microprocessor under the control of a software program that is capable of processing signal from the site and determining the pulse or determining a magnitude associated with the pulse, or a statistically relevant value thereof, of the site based upon the measured intensities of the reflected light and may also perform the steps necessary to compare such a pulse value to a predetermined value or to pulse values of various tested sites.

B. Hemoglobin Characterization Element

In certain embodiments of the subject invention, the sample type characterization element includes a hemoglobin characterization element capable of determining the characteristic of hemoglobin of a site. In particular, the hemoglobin characterization element is configured to determine the total hemoglobin level of the site and/or determine the amount of oxygenated hemoglobin to deoxygenated hemoglobin or the HbO/Hb ratio.

The hemoglobin characterization element is typically an optics element, where such an optics element contains (1) at least one light source such as at least one of the following: a light emitting diode (LED), a light emitter, a bispectral emitter, a dual spectral emitter, a photoemitter, a photodiode, a semiconductor die, laser, or the like, and (2) at least one detector capable of measuring light absorbed by the site, i.e., intercepting light transmitted through or reflected from a surface upon which the light source is focused, and which may also capable of converting such light into measurable electrical signals, e.g., voltage, current, etc.), where suitable detectors include, but are not limited to, at least one of the following: a photodiode, a photoelectric receiver, a photodetector, a semiconductor die, or the like. As noted above, light sources and detectors are commonly known in the art, where examples of suitable light sources and detectors suitable for use with the present invention include those disclosed in U.S. Pat. Nos. 6,241,680 and 6,233,266, the disclosures of which are herein incorporated by reference.

Typically, the at least one light source of relatively narrow wavelength distribution, e.g., at least one LED or laser, will be capable of irradiating a prospective sampling site with at least one wavelength, typically at least two wavelengths ranging from about 400–1200 nm. In other words, if one light source is used and more than one wavelength is required, the one light source will be capable of producing or emitting light at more than one wavelength. If more than one light source is used, at least two of such light sources will be capable of transmitting light at different wavelengths either serially or simultaneously with respect to each other. The at least one light source and/or the associated detector(s) may be positioned at or near the proximal end of the housing, i.e., the portion of the housing in close proximity to or in direct contact with the skin of the user. In other words, the light source(s) and/or detector(s) may be located near the proximal orifice of the device; however, the light source(s) and /or detector(s) may be positioned elsewhere in the device as well.

The hemoglobin characterization element may be operatively associated with a microprocessor under the control of a software program that is capable of processing signal from the site and determining total hemoglobin or the components thereof (oxygenated or deoxygenated Hb) or the HbO/Hb ratio, or a statistically relevant value thereof, of the site based upon the measured absorbances of the light and may also be operatively associated with measurement processing means for performing the steps necessary to compare such hemoglobin values to a predetermined value or to hemoglobin values of various tested sites.

III. Measurement Processing Components

The device also includes associated electronics for processing the measurements or signals produced by the site flow characterization element and/or the sample type characterization element and/or may be used to automatically determine the concentration of an analyte in the sample, as described below. For example, in many embodiments the device may also includes a current to voltage converter unit and an analog to digital converter, where such electronics are known in the art.

Furthermore, the device includes a microprocessor working under the control of a software program, where such a software program contains the entire code necessary for the microprocessor to perform all of the tasks required by the device, e.g., the microprocessor contains all the code necessary for determining the suitability of a sampling site and/or the concentration of an analyte. In other words, the program code of the software instructs the microprocessor to carry out all the steps which are necessary for it to determine one or more of the site's functions, such as the flow characteristics of the site, and/or the sample type characteristics, i.e., whether the site include primarily arterial/capillary, venous or interstitial fluid, the appropriateness of the site for a particular test and the concentration of at least one analyte in the sample, among other functions such as automatically activating the device, etc.

IV. Skin Piercing Element

The device may further include at least one skin-piercing element, e.g., a needle or the like, for accessing and withdrawing or collecting the targeted sample fluid. The at least one skin-piercing element may be associated with an actuating mechanism, such as a spring-loaded mechanism, for manually actuating the at least one skin-piercing element towards the skin; however, the at least one skin-piercing element may also be capable of being activated automatically. Representative lancing elements adaptable for use with the present invention include, but are not limited to, those disclosed in U.S. Pat. Nos. 4,449,529; 4,892,097; 5,314,441; 5,318,54; 5,366,469; 5,395,388; 5,439,473; 5,454,828 5,540,709, 6,197,040; 6,071,294; 6,045,567 and 6,036,924, the disclosure of which are herein incorporated by reference. Furthermore, the Penlet® brand Blood Samplers manufactured by LifeScan, Inc. are also adaptable for use with the present invention. The at least one skin-piercing element may further include a fluid pathway or channel operatively associated with, e.g., either within, concentric with or adjacent to, the at least one skin-piercing element for transporting fluid accessed by the element.

The at least one skin-piercing element may also include one or more fluid enhancing elements for stimulating the production or expression of physiological fluid from the site. For example, a vibration element may be operatively associated with the present device or with the at least one skin-piercing element of the device, where such a vibration device is capable of vibrating at a frequency in the range of about 10 to 1000 Hz. In certain embodiments, the fluid enhancing means may include, in addition to or in place of other fluid stimulating elements, a temperature element to increase the temperature of the site to stimulate fluid expression.

V. Test Strips

The device may be adapted to receive or otherwise be operatively associated or in communication with standard analyte concentration determination test strips, e.g., glucose reagent test strips. In many devices of the subject methods, one or more test strips are capable of being loaded directly into the device, i.e., the present device is configured to receive at least one test strip, before, during or after the physiological sample is extracted. Examples of such a reagent test strips suitable for use with the subject invention include those described in copending U.S. application Ser. Nos. 09/333,793; 09/497,304; 09/497,269; 09/736,788 and 09/746,116, and U.S. Pat. Nos. 5,563,042; 5,753,452; 5,789,255, the disclosures of which are herein incorporated by reference.

In those embodiments where a reagent test strip is in communication with the device, an element for automatically determining the concentration of an analyte in a physiological sample may also be included in the device, where such automatic elements, e.g., automatic meters, are well known in the art. Examples of such automatic elements adaptable for use with the present invention include those described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836; 5,972,294 and described in copending U.S. application Ser. Nos. 09/333,793; 09/497,304; 09/497,269; 09/736,788 and 09/746,116, the disclosures of which are herein incorporated by reference.

Figure 3:
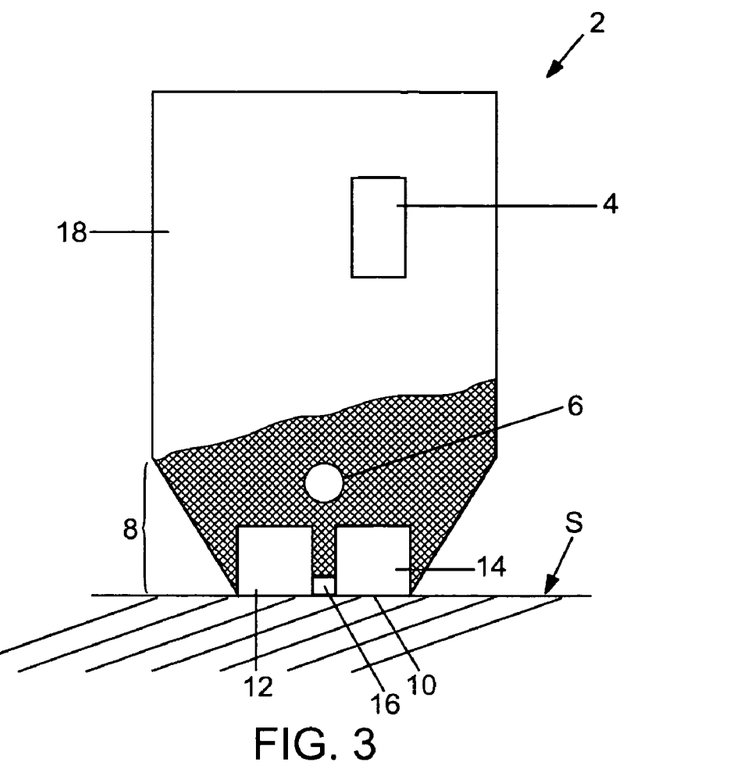
FIG. 3 shows an embodiment of an exemplary device of the subject invention showing a cut-away view of the proximal portion of the device.

Referring now to the drawings, FIG. 3 provides a representation of an exemplary device of the subject invention showing a cut-away view of the proximal portion of the device. FIG. 3 shows device 2 made-up of an outer housing 18, which includes a visual display or liquid crystal display 4 for displaying results to a user of the device (as mentioned above, information may also be audibly communicated to the user in stead or in addition to being visually displayed) and a proximal orifice 10, where the proximal orifice of the device 2 is in communication with, or is in close proximity to, an area of skin S. A cut-away view of the proximal portion 8 of the device 2 reveals the inner components of the subject device. Accordingly, device 2 includes flow characterization element 12, sample type characterization element 14, temperature sensor 16 and microprocessor 6.

Figure 4:
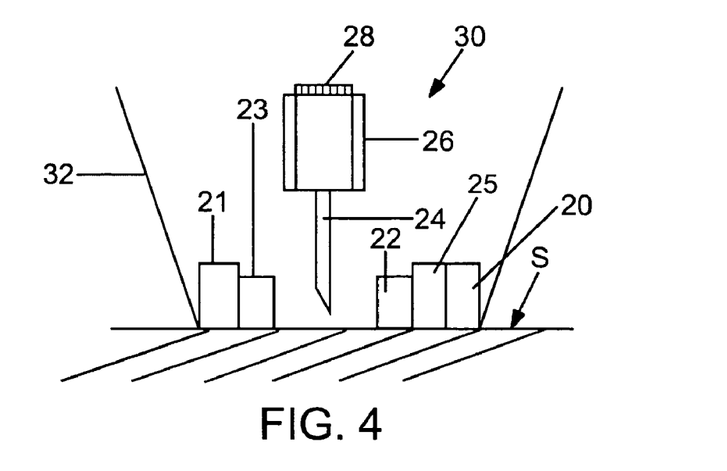
FIG. 4 shows an embodiment of an exemplary proximal portion of a device of subject invention.

FIG. 4 provides a representation of an exemplary proximal portion of the subject device, showing a cut-away view of the proximal portion. In this particular embodiment, the proximal portion 32 of the device 30 is shown, where a proximal portion 32 of device 30 includes a flow characterization element made up of temperature characterization element 22 and a sample type characterization element which includes laser diode 20 and laser diode 21 and detectors 23 and 25. Further included in this embodiment is at least one skin-piercing element 24, operatively associated with spring mechanism 26. Device 30 includes reagent test strip 28, where test strip 28 may be in communication with an internal lumen of the at least one skin-piercing element 24 (not shown) or some other elongated tube or transfer element, through which sample is drawn to the test strip 28. It will be apparent, however, that test strip 28 may be separate from and/or otherwise adjacent to the skin-piercing element 24.

Kits

Also provided by the subject invention are kits for use in practicing the subject methods. The kits of the subject invention include at least one subject device, where such a device includes at least one flow characterization element for characterizing the flow of a potential physiological sampling site and/or may include a sample type characterization element for determining the type of fluidic contents of the site. Oftentimes the kits of the subject invention include a plurality of such devices. The kits may also include a reusable or disposable lancing element, if not already integrated into the device. Furthermore, the kit may also include a reusable or disposable meter, if not already integrated into the device, that may be used with reusable or disposable test strips used with the subject invention. Certain kits may include various types of test strips, e.g., where various test strips contain the same or different reagents, e.g., electrochemical and/or colorimetric test strips. Finally, the kits may further include instructions for using the subject devices for determining a suitable physiological fluid sampling site and/or for determining the concentration of at least one analyte in a physiological sample. The instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc.

Experimental

The following example correlating skin temperature with fluid volume is offered by way of illustration and not by way of limitation.

A fine thermocouple (0.002 inch type CHAL from Omega Technologies Corp.), associated at the end of a Penlet® Plus Blood Sampler using a FinePoint™ lancet from LifeScan, Inc., was used to measure the temperature of a sampling site and to access and obtain sample therefrom. As such, the thermocouple was positioned in the center of the orifice of the Blood Sampler having a variable depth setting fixed to 6. A location on the upper forearm of a subject was chosen as a sampling site. The temperature of the site was measured and the site was lanced substantially immediately thereafter. Sample which was readily expressed for a period of about 30 seconds was collected and the weight thereof was determined. This procedure was repeated for a sample size of 21.

Figure 5:
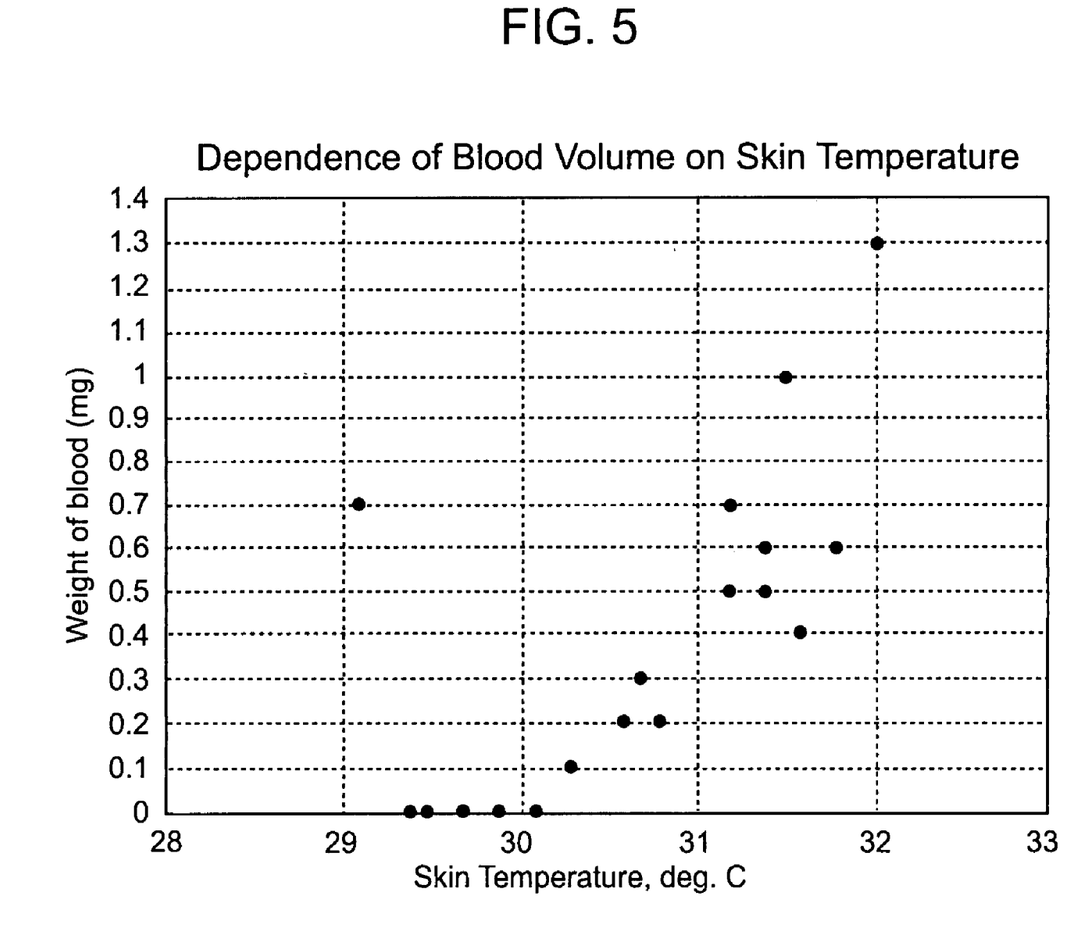
FIG. 5 shows a graph correlating temperature at a site to the amount of sample expressed therefrom.

FIG. 5 shows the results of the amount of blood volume, represented by sample weight, collected for each temperature. The graph shows that there is a clear correlation between temperature of a site and the weight or volume of sample obtainable therefrom. There is one outlier at about 29.1° C., which may be attributed to a deeper lancing depth or the like.

It is evident from the above description and discussion that the above described invention provides a simple, quick and convenient way to locate a suitable physiological fluid sampling site, obtain a physiological sample from the suitable site and determine an analyte concentration thereof. The above described invention provides a number of advantages, including ease of use, a single skin-piercing event, non-invasiveness and compatibility with both electrochemical and colorimetric analyte concentration characterization assays. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for determining the suitability of a site for sampling physiological fluid for use in an analyte concentration determination test, said method comprising the steps of
   (a) contacting a potentially suitable site with a device configured to determine the type of physiological fluid at said potentially suitable site;
   (b) determining the type of physiological fluid at said potentially suitable site; and
   (c) determining whether said potentially suitable site is suitable for sampling physiological fluid for use in said analyte concentration determination test, based on said determined fluid type.

2. The method according to claim 1, wherein said step of determining the type of physiological fluid at said potentially suitable site comprises characterizing the hemoglobin of the physiological fluid at said potentially suitable site.

3. The method according to claim 2, wherein the step of characterizing the hemoglobin comprises determining the hemoglobin concentration of said physiological fluid at said potentially suitable site.

4. The method according to claim 2, wherein the step of characterizing the hemoglobin comprises determining the concentration of the oxygenated hemoglobin and deoxygenated hemoglobin.

5. The method according to claim 2, wherein the step of characterizing the hemoglobin comprises determining the ratio of oxygenated hemoglobin to deoxygenated hemoglobin.

6. The method according to claim 1, further comprising the step of characterizing the flow of physiological fluid at said potentially suitable site.

7. The method according to claim 6, wherein said step of characterizing the flow comprises determining the temperature at said potentially suitable site.

8. A method for determining the suitability of a site for sampling physiological fluid for use in an analyte concentration determination test, said method comprising the steps of:
   (a) contacting a potentially suitable site with a device configured to determine the type of physiological fluid at said potentially suitable site;
   (b) determining the type of physiological fluid at said potentially suitable site by characterizing the pulse of said potentially suitable site; and
   (c) determining whether said potentially suitable site is suitable for sampling physiological fluid for use in said analyte concentration determination test, based on said determined fluid type.

9. The method according to claim 8, wherein the step of characterizing the pulse of said site comprises characterizing the red blood cells of said physiological fluid at said potentially suitable site.

10. The method according to claim 9, wherein the step of characterizing red blood cells comprises characterizing red blood cell flux.

11. The method according to claim 8, further comprising the step of determining the concentration of at least one analyte in said physiological fluid.

12. The method according to claim 11, wherein said concentration determination comprises transferring a volume of said physiological fluid to an analyte concentration test strip.

13. The method according to claim 11, wherein said at least one analyte is glucose and said physiological fluid is blood.

14. The method according to claim 11, wherein an automated meter performs said concentration determination automatically.

15. The method according to claim 8, wherein said at least one analyte is glucose and said physiological fluid is interstitial fluid.

16. A method for determining the suitability of a site for sampling physiological fluid for use in an analyte concentration determination test, said method comprising the steps of:
   (a) contacting a potentially suitable site with a device configured to determine the type of physiological fluid at said potentially suitable site;
   (b) determining the type of physiological fluid at said potentially suitable site;
   (c) determining whether said potentially suitable site is suitable for sampling physiological fluid for use in said analyte concentration determination test, based on said determined fluid type; and
   (d) characterizing the flow of said physiological fluid at said potentially suitable site by characterizing the red blood cells of said physiological fluid.

17. A method for determining the suitability of a site for sampling physiological fluid for use in an analyte concentration determination test, said method comprising the steps of:

(a) contacting a potentially suitable site with a device configured to determine the type of physiological fluid at said potentially suitable site;
(b) determining the type of physiological fluid at said potentially suitable site;
(c) determining whether said potentially suitable site is suitable for sampling physiological fluid for use in said analyte concentration determination test, based on said determined fluid type; and
(d) determining the concentration of at least one analyte in said physiological fluid wherein said at least one analyte is glucose and said physiological fluid is interstitial fluid.

18. The method according to claim 17, further comprising the step of stimulating the site to enhance the volume of physiological fluid expressed from said site.

* * * * *